(12) United States Patent
Okumura et al.

(10) Patent No.: US 9,610,033 B2
(45) Date of Patent: Apr. 4, 2017

(54) SENSOR CHIP, DETECTION METHOD, AND DETECTION APPARATUS

(71) Applicant: PANASONIC CORPORATION, Osaka (JP)

(72) Inventors: Yasuaki Okumura, Kyoto (JP); Tatsurou Kawamura, Kyoto (JP); Masaru Minamiguchi, Kyoto (JP); Masahiko Shioi, Kyoto (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 14/951,301

(22) Filed: Nov. 24, 2015

(65) Prior Publication Data

US 2016/0073938 A1    Mar. 17, 2016

Related U.S. Application Data

(63) Continuation of application No. PCT/JP2014/002832, filed on May 28, 2014.

(30) Foreign Application Priority Data

Jun. 4, 2013   (JP) ................................ 2013-117587

(51) Int. Cl.
 *G01J 3/44*    (2006.01)
 *A61B 5/1459*   (2006.01)
 (Continued)

(52) U.S. Cl.
 CPC ......... *A61B 5/1459* (2013.01); *G01N 21/554* (2013.01); *G01N 21/658* (2013.01)

(58) Field of Classification Search
 CPC ............. A61B 5/14865; G01N 21/658; G01N 21/554; G01N 2021/258
 See application file for complete search history.

(56) References Cited

U.S. PATENT DOCUMENTS

2004/0199062 A1*  10/2004  Petersson ........... A61B 5/14532
                                                                600/316
2008/0188723 A1*  8/2008  Kristensen ....... G01N 33/54373
                                                                600/316

FOREIGN PATENT DOCUMENTS

JP    2005-342134 A    12/2005
WO    2008/146569 A1   12/2008
WO    2011/053247 A1    5/2011

OTHER PUBLICATIONS

Yuen, J.M. et al., "Transcutaneous Glucose Sensing by Surface-Enhanced Spatially Offset Raman Spectroscopy in a Rat Model". Letters to Analytical Chemistry. vol. 82, No. 20. Oct. 15, 2010. pp. 8382-8385.

(Continued)

*Primary Examiner* — Kara E Geisel
*Assistant Examiner* — Maurice Smith
(74) *Attorney, Agent, or Firm* — McDermott Will & Emery LLP

(57) ABSTRACT

An exemplary sensor chip includes a substrate, a metal pattern, a proximate substance, and a light shielding layer. The metal pattern is on the substrate. The proximate substance is on or near the metal pattern. The light shielding layer is provided on the substrate so as to cover the metal pattern and the proximate substance. The light shielding layer is a layer that blocks the excitation light from going into the proximate substance, and is made of a substance which becomes degraded inside a subject.

12 Claims, 6 Drawing Sheets

(51) Int. Cl.
*G01N 21/552* (2014.01)
*G01N 21/65* (2006.01)

(56) References Cited

OTHER PUBLICATIONS

Lyandres, O. et al. "Real-Time Glucose Sensing by Surface-Enhanced Raman Spectroscopy in Bovine Plasma Facilitated by a Mixed Decanethiol/Mercaptohexanol Partition Layer". Analytical Chemistry, vol. 77, No. 19. Oct. 1, 2005. pp. 6134-6139.
Minamiguchi, M. et al. "Biosensing with Surface Enhanced Raman Spectroscopy". Panasonic Technical Journal vol. 57, No. 3. Oct. 2011. pp. 33-34. (w/ English abstract).
International Search Report mailed Aug. 26, 2014, issued in corresponding International Appliation No. PCT/JP/2014/002832. (w/ English translation).

\* cited by examiner

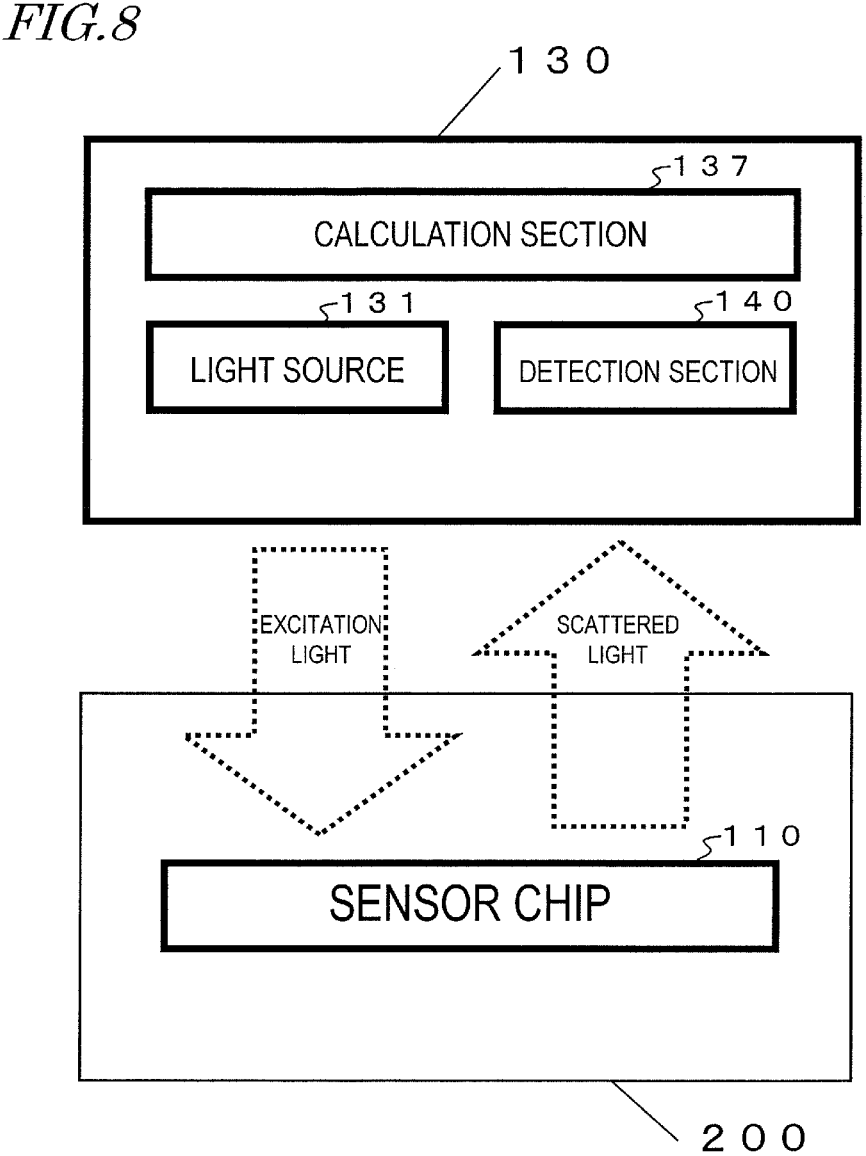

SENSOR CHIP, DETECTION METHOD, AND DETECTION APPARATUS

This is a continuation of International Application No. PCT/JP2014/002832, with an international filing date of May 28, 2014, which claims priority of Japanese Patent Application No. 2013-117587, filed on Jun. 4, 2013, the contents of which are hereby incorporated by reference.

BACKGROUND

1. Technical Field

The present application relates to a sensor chip, a detection method, and a detection apparatus for detecting an analyte based on surface-enhanced Raman spectroscopy.

2. Description of the Related Art

In Raman spectroscopy, a substance is irradiated with monochromatic light (excitation light) of a certain frequency so that scattered light occurs therefrom, and any scattered light that has a different frequency (hereinafter referred to as Raman-scattered light) from the frequency of the incident light is spectroscopically detected. A difference (Raman shift) between the frequency of the Raman-scattered light and the frequency of the incident light is equal to the frequency which corresponds to the difference between energy levels of vibration or rotation of molecules and atoms in the molecule or crystal that composes a substance, and takes a value which is specific to the structure of the substance. Therefore, Raman spectroscopy is utilized to discover the structure and state of a molecule.

Among other Raman spectroscopy techniques, surface-enhanced Raman spectroscopy has been proposed, which utilizes surface-enhanced Raman scattering (SERS). Surface-enhanced Raman scattering is a phenomenon in which Raman-scattered light from molecules that have adhered to the surface of a specially-designed sensor chip having a precious metal structure of nanometer size increases in intensity. Surface-enhanced Raman scattering provides an enhancement of usually about $10^4$ to $10^9$. This enables highly sensitive detection of molecules which are immobilized on a metal surface, or even molecules near the metal surface.

In the field of medical diagnosis, a wide range of applications of surface-enhanced Raman spectroscopy is being considered. Surface-enhanced Raman spectroscopy is especially applied to the detection of biological components such as glucose that is contained in a biological body. Furthermore, based on an intensity of surface-enhanced Raman-scattered light, the concentration of a biological component can be calculated.

J. M. Yuen, N. C. Shah et. al., Anal. Chem. (2010) 82: 8382-8385 discloses a method of measuring in vivo the glucose concentration in a biological body through surface-enhanced Raman spectroscopy, by using a sensor chip which is embedded in a biological body. With such an approach, where a miniaturized sensor chip is completely embedded in a biological body, it becomes possible to measure or monitor an object of analysis by merely radiating light from the exterior upon need of measurement, without inflicting pain each time.

SUMMARY

In the aforementioned approach, it is necessary to embed a sensor chip inside a subject (an object of analysis)(e.g., within a biological body). A possible way of embedding a sensor chip inside a subject (e.g., within a biological body) may be surgical embedment; that is, skin is incised, and a sensor chip is embedded in a biological body through the site of incision. Another way may be to utilize an embedding jig which is specialized for the sensor chip.

Conventionally, a sensor chip has a metal pattern layer which is formed on the sensor chip surface, the metal pattern layer being capable of inducing a surface plasmon wave. Since the metal pattern layer is composed of minute structures of metal, it has poor physical durability. Therefore, when the aforementioned sensor chip is embedded inside a subject, due to contact between the sensor plane and the specialized embedding jig, and further due to contact between the sensor plane and the subject (e.g., biological tissue), the metal minute structures may be destroyed. This has resulted in the problem of a reduced sensor sensitivity and a shorter sensor life inside the subject.

One non-limiting, and exemplary embodiment provides a sensor chip for detecting an analyte inside a subject, comprising a substrate, a metal pattern, a proximate substance, and a light shielding layer, the metal pattern being on one face of the substrate, and the proximate substance being on or near the metal pattern, wherein, the metal pattern induces a surface plasmon wave by being irradiated with excitation light; the proximate substance generates first surface-enhanced Raman-scattered light by being irradiated with the excitation light, the first surface-enhanced Raman-scattered light having a first peak; the first surface-enhanced Raman-scattered light does not vary with changes in the concentration of the analyte; the proximate substance is a substance which binds to the analyte; the proximate substance having bound to the analyte generates second surface-enhanced Raman-scattered light by being irradiated with the excitation light, the second surface-enhanced Raman-scattered light having a second peak different from the first peak; the second surface-enhanced Raman-scattered light varies with changes in the concentration of the analyte; the light shielding layer is provided on the substrate so as to cover the metal pattern and the proximate substance; the light shielding layer is a layer which blocks the excitation light from going into the proximate substance; and the light shielding layer is made of a substance which becomes degraded inside the subject.

According to an embodiment of the present invention, a sensor chip is restrained from being damaged when embedded inside a subject. As a result, an analyte that is contained in, for example, a biological body or a subject solution (e.g., a biological component such as glucose) can be detected more accurately.

These general and specific aspects may be implemented using a device, a system, and a method, and any combination of devices, systems, and methods.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 8 is a diagram showing an exemplary construction for a detection apparatus according to Embodiment 3.

DETAILED DESCRIPTION

Figure 1:
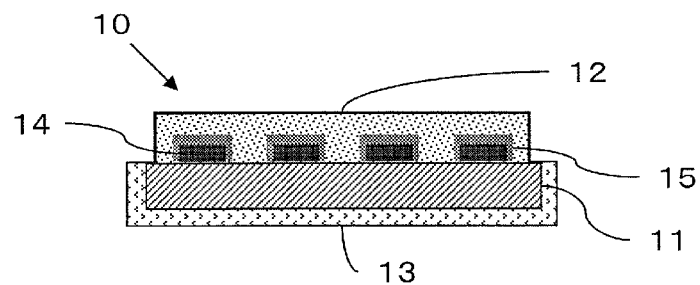
FIG. 1 is a diagram showing an exemplary construction for a sensor chip according to Embodiment 2.

First, one implementation of the present invention will be described in outline.

A sensor chip as one implementation of the present invention is a sensor chip for detecting an analyte inside a subject, comprising a substrate, a metal pattern, a proximate substance, and a light shielding layer, the metal pattern being on one face of the substrate, and the proximate substance being on or near the metal pattern, wherein, the metal pattern induces a surface plasmon wave by being irradiated with excitation light; the proximate substance generates first surface-enhanced Raman-scattered light by being irradiated with the excitation light, the first surface-enhanced Raman-scattered light having a first peak; the first surface-enhanced Raman-scattered light does not vary with changes in the concentration of the analyte; the proximate substance is a substance which binds to the analyte; the proximate substance having bound to the analyte generates second surface-enhanced Raman-scattered light by being irradiated with the excitation light, the second surface-enhanced Raman-scattered light having a second peak different from the first peak; the second surface-enhanced Raman-scattered light varies with changes in the concentration of the analyte; the light shielding layer is provided on the substrate so as to cover the metal pattern and the proximate substance; the light shielding layer is a layer which blocks the excitation light from going into the proximate substance; and the light shielding layer is made of a substance which becomes degraded inside the subject.

[0018-0020] Air voids may be dispersed in the light shielding layer. The analyte may be glucose. The proximate substance may be a phenylboronic acid compound having a thiol group at one end. The phenylboronic acid compound may be chemisorbed to a surface of the metal pattern via the thiol group.

The first peak of the first surface-enhanced Raman-scattered light may have the peak position 1073 $cm^{-1}$. The second peak of the second surface-enhanced Raman-scattered light may have the peak position 997 $cm^{-1}$.

The subject may be a biological body. The light shielding layer may be made of a first biocompatible polymer which is biodegradable. Another face of the substrate not having the metal pattern thereon may be coated with a second biocompatible polymer which is not biodegradable. The light shielding layer may be a light scattering layer which scatters the excitation light.

A detection method as another implementation of the present invention is a detection method for detecting the analyte by using any of the above sensor chips, comprising the following steps (a) to (g): step (a) of providing a detection apparatus, the detection apparatus including a light source for emitting the excitation light, a detector, and a calculation circuit; step (b) of embedding the sensor chip inside a subject; step (c) of irradiating the sensor chip embedded inside the subject with the excitation light from the light source to generate first surface-enhanced Raman-scattered light; step (d) of detecting the first surface-enhanced Raman-scattered light occurring at step (c) with the detector to obtain a first intensity Xa; step (e) of determining with the calculation circuit whether or not the first intensity Xa is equal to or greater than a predetermined intensity Xz; step (f) of, after determining at step (e) that the first intensity Xa is equal to or greater than the predetermined intensity Xz, irradiating the sensor chip embedded inside the subject with the excitation light from the light source to generate second surface-enhanced Raman-scattered light; and step (g) of detecting the second surface-enhanced Raman-scattered light occurring at step (f) with the detector to obtain a second intensity Xb.

The detection apparatus further may include a memory for retaining information representing correlation between the second intensity Xb and analyte concentration. A concentration of the analyte may be calculated based on the second intensity Xb obtained at step (g) and on the information.

A detection apparatus as still another implementation of the present invention is a detection apparatus for detecting the analyte by using any of the above sensor chips, comprising: a light source for emitting the excitation light, a detector, and a calculation circuit, wherein, the detection apparatus irradiates the sensor chip embedded inside a subject with the excitation light from the light source to generate first surface-enhanced Raman-scattered light, the detector detects the generated first surface-enhanced Raman-scattered light to obtain a first intensity Xa, the calculation circuit determines whether or not the first intensity Xa is equal to or greater than a predetermined intensity Xz; after determining that the first intensity Xa is equal to or greater than the predetermined intensity Xz, the detection apparatus irradiates the sensor chip embedded inside the subject with the excitation light from the light source to generate second surface-enhanced Raman-scattered light; and the detector detects the generated second surface-enhanced Raman-scattered light to obtain a second intensity Xb.

The detection apparatus further may comprise a memory for retaining information representing correlation between the second intensity Xb and analyte concentration. The detection apparatus may calculate a concentration of the analyte based on the second intensity Xb obtained by detecting the generated second surface-enhanced Raman-scattered light with the detector and on the information.

A method of controlling a detection apparatus as still another implementation of the present invention is a method of controlling a detection apparatus which detects the analyte by using any of the above sensor chips, the detection apparatus including a light source for emitting the excitation light, a detector, and a calculation circuit, the method comprising: step (A) of irradiating the sensor chip embedded inside a subject with the excitation light from the light source to generate first surface-enhanced Raman-scattered light; step (B) of detecting the first surface-enhanced Raman-scattered light occurring at step (A) with the detector to obtain a first intensity Xa; step (C) of determining with the calculation circuit whether or not the first intensity Xa is equal to or greater than a predetermined intensity Xz; step (D) of, after determining at step (C) that the first intensity Xa is equal to or greater than the predetermined intensity Xz, irradiating the sensor chip embedded inside the subject with the excitation light from the light source to generate second surface-enhanced Raman-scattered light; and step (E) of detecting the second surface-enhanced Raman-scattered light occurring at step (D) with the detector to obtain a second intensity Xb.

Hereinafter, embodiments of the present invention will be described with reference to the drawings. Note that the component elements shown in the figures are not necessary drawn to scale, but may be exaggerated in order to clearly illustrate the principles of the present invention.

Embodiment 1

Embodiment 1 will be described with reference to FIG. 6.

Figure 6:
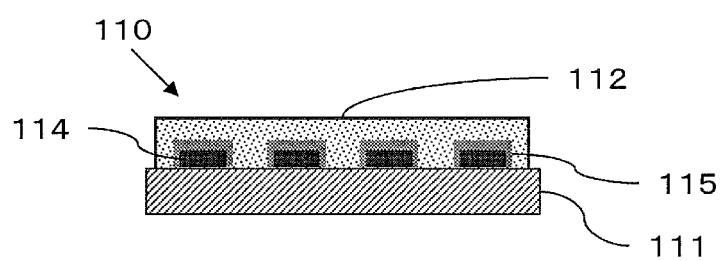
FIG. 6 shows an exemplary construction for a sensor chip according to Embodiment 1.

FIG. 6 is a diagram showing a sensor chip 110 according to Embodiment 1. The sensor chip 110 of Embodiment 1 is a sensor chip which detects an analyte inside a subject. The sensor chip 110 may be embedded in the subject.

The sensor chip 110 includes a substrate 111, a metal pattern 114, a proximate substance 115, and a light shielding layer 112. The metal pattern 114 is provided on the substrate 111. The metal pattern 114 induces a surface plasmon wave by being irradiated with excitation light.

The proximate substance 115 is provided on or near the metal pattern 114. When irradiated with excitation light, the proximate substance 115 generates first surface-enhanced Raman-scattered light having a first peak. The first surface-enhanced Raman-scattered light does not vary with changes in the concentration of the analyte.

Moreover, the proximate substance 115 is a substance that binds to the analyte. When irradiated with excitation light, the proximate substance 115 having bound to the analyte generates second surface-enhanced Raman-scattered light having a second peak different from the first peak. The second surface-enhanced Raman-scattered light varies with changes in the concentration of the analyte.

The light shielding layer 112 is provided on the substrate 111 so as to cover the metal pattern 114 and the proximate substance 115. The light shielding layer 112 is a layer that blocks excitation light from going into the proximate substance 115. The light shielding layer 112 is made of a substance that becomes degraded within the subject.

With the above construction, the light shielding layer 112 reduces damage to the metal pattern 114 during embedment of a sensor chip into the subject. The proximate substance 115 allows it to be determined whether the light shielding layer 112 has been degraded inside the subject or not, by utilizing scattered light from the proximate substance 115. This ensures that analyte detection and/or measurement of analyte concentration are performed after the light shielding layer 112 is degraded inside the subject. Since the light shielding layer 112 is a layer that blocks excitation light from going into the proximate substance 115, it is possible to determine whether or not the light shielding layer 112 has been degraded inside the subject with an improved accuracy, by utilizing scattered light from the proximate substance 115. In other words, analyte detection can be prevented when the light shielding layer 112 has not been degraded inside the subject, for example.

In the sensor chip 110 of Embodiment 1, air voids may be dispersed in the light shielding layer 112. By dispersing air voids in the light shielding layer 112, it becomes possible to degrade the light shielding layer 112 inside the subject with more ease and in shorter time. In Embodiment 1, the analyte may be glucose.

In the sensor chip 110 of Embodiment 1, the proximate substance 115 may be a phenylboronic acid compound having a thiol group at one end. The phenylboronic acid compound may be chemisorbed to the surface of the metal pattern 114 via the thiol group.

In this case, the first peak of the first surface-enhanced Raman-scattered light has the peak position 1073 $cm^{-1}$.

Moreover, the second peak of the second surface-enhanced Raman-scattered light has the peak position 997 $cm^{-1}$.

In Embodiment 1, the subject may be a biological body (e.g., a human or an animal). The light shielding layer 112 may be made of a first biocompatible polymer which is biodegradable. The other face of the substrate 111 not having the metal pattern 114 thereon may be coated with a second biocompatible polymer which is not biodegradable. In the sensor chip 110 of Embodiment 1, the light shielding layer 112 may be a light scattering layer that scatters excitation light.

As a more specific exemplary construction for the sensor chip 110 of Embodiment 1, a sensor chip according to Embodiment 2 will be described below.

Embodiment 2

Embodiment 2 will be described with reference to FIG. 1 to FIG. 5, and FIG. 7. In Embodiment 2, an analyte detection method by using the sensor chip 110 described in Embodiment 1 is proposed.

Embodiment 2 illustrates the sensor chip 10 shown in FIG. 1 as a typical example of the sensor chip 110. Embodiment 2 illustrates a biological body as the subject. Embodiment 2 illustrates glucose as the analyte. Moreover, a phenylboronic acid compound is illustrated as the proximate substance. In Embodiment 2, a light scattering layer is illustrated as the light shielding layer.

Figure 7:
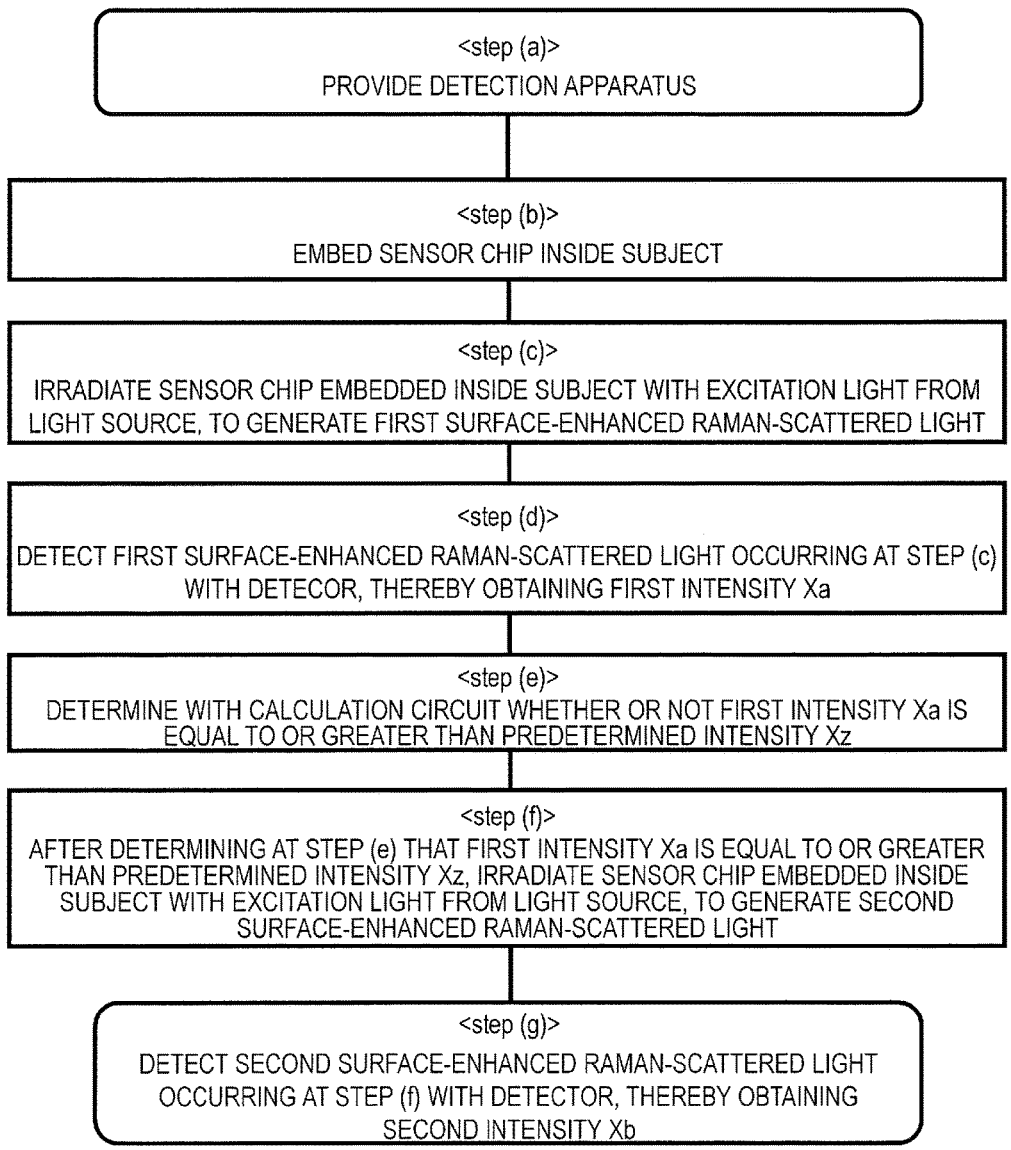
FIG. 7 is an illustrative flowchart of a detection method according to Embodiment 2.

FIG. 7 is an illustrative flowchart of the detection method according to Embodiment 2. The detection method of Embodiment 2 includes steps (a) to (g) as described below. With the detection method of Embodiment 2, by utilizing scattered light from the proximate substance, it can be determined whether the light shielding layer has been degraded inside the subject or not. In doing so, obtaining a second intensity Xb (described later) after the light shielding layer is degraded inside the subject makes for a more accurate analyte detection.

<Step (a)>

Step (a) is a step of providing a detection apparatus. Herein, the detection apparatus includes a light source and a detector. Hereinafter, step (a) according to Embodiment 2 will be described in detail.

At step (a), a detection apparatus is provided. The detection apparatus 30 shown in FIG. 3 includes a light source 31 and a spectrometer 36 as one example of the detector. As necessary, the detection apparatus 30 includes a bandpass filter 32, an optical system 35, a beam splitter 34, a memory 38, and a calculation circuit 37.

Excitation light 33 from the light source 31 is substantially parallel light having a wavelength of 785 nm, for example. An example of the substantially parallel light is light having a circular beam shape with a diameter of 100 µm. The bandpass filter 32 only allows the excitation light 33 from the light source 31 to pass therethrough.

The optical system 35 shapes the surface-enhanced Raman-scattered light occurring from a sensor chip 10 into a beam. The optical system 35 may include one or more lenses. In the example shown in FIG. 3, the sensor chip 10 is located inside the skin tissue 20.

The beam splitter 34 allows surface-enhanced Raman-scattered light 39 occurring from the sensor chip 10 to be led into the spectrometer 36. The spectrometer 36, which exemplifies the detector, detects the surface-enhanced Raman-scattered light 39. The spectrometer 36 outputs a signal which is in accordance with the detected light. The spectrometer 36 may have a plurality of photosensitive regions.

The calculation circuit 37 (e.g., a computer) calculates the intensity of the light which is detected by the spectrometer 36. From the calculated intensity, it calculates the concentration of the analyte, for example.

<Step (b)>

Step (b) is a step of embedding a sensor chip inside the subject (e.g., within a biological body). One way of embedding a sensor in a biological body may be surgical embedding; that is, skin is incised, and a sensor chip is embedded in a biological body through the site of incision. Another way may be to utilize a specialized embedding jig that is adapted to the shape of the sensor chip and its site of embedment.

Figure 2:
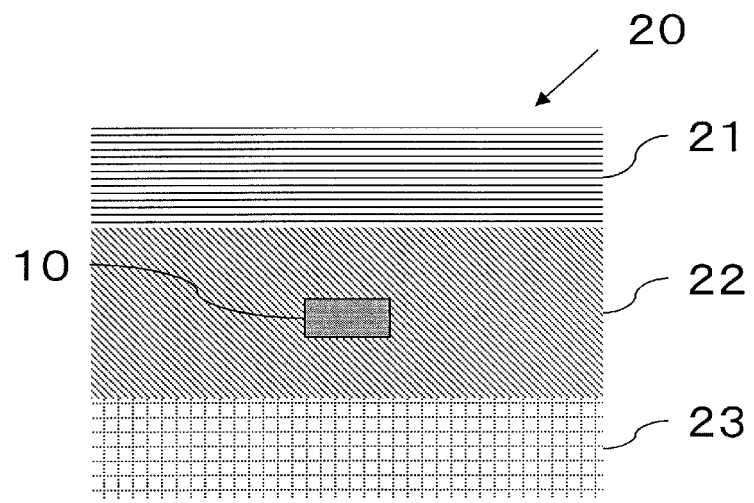
FIG. 2 is a schematic cross-sectional view of skin tissue.

FIG. 2 schematically shows an enlarged cross-sectional view of skin tissue 20. As shown in FIG. 2, the skin tissue 20 includes epidermal tissue 21, dermis tissue 22, and subcutaneous tissue 23. The epidermal tissue 21, dermis tissue 22, and subcutaneous tissue 23 are layered in this order.

The epidermal tissue 21 is located at the surface of the biological body. The epidermal tissue 21 has a thickness of approximately 0.2 mm to 0.5 mm. The dermis tissue 22 has a thickness of approximately 0.5 mm to 2 mm. The subcutaneous tissue 23 is mainly composed of fat tissue.

The sensor chip 10 is embedded in the dermis tissue 22, for example. The sensor chip 10 is retained in a manner of being immersed in the interstitial fluid, which is a bodily fluid existing between tissue cells. The term "bodily fluid" used in the present specification means an interstitial fluid.

The dermis tissue 22 includes plural capillary blood vessels. Therefore, bodily fluids contain biological components from the capillary blood vessels. In particular, the walls of capillary blood vessels have a high permeability with respect to glucose. Therefore, a glucose concentration in the bodily fluid is highly correlated with the blood glucose level.

<Step (c)>

Step (c) is a step of irradiating the sensor chip, which has been embedded inside the subject, with excitation light from the light source to generate first surface-enhanced Raman-scattered light. Hereinafter, step (c) in Embodiment 2 will be described in detail.

In step (c), excitation light 33 from the light source 31 is transmitted through the biological surface (skin), for example. As the sensor chip 10 having been embedded within a biological body (e.g., dermis tissue 22) is irradiated with the transmitted excitation light 33, surface-enhanced Raman-scattered light 39 occurs.

The surface-enhanced Raman-scattered light 39 includes first surface-enhanced Raman-scattered light. In this example, as shown in FIG. 2, the sensor chip 10 is embedded in the dermis tissue 22 so that its face having the metal pattern 14 thereon lies generally parallel to the epidermal tissue 21. The distance from the epidermal tissue 21 to the sensor chip 10 is approximately 1.5 mm, for example.

An exemplary construction of the sensor chip according to Embodiment 2 of the present invention will be described with reference to FIG. 1. In an embodiment of the present invention, there is no particular limitation as to the substrate 11 so long as it is a substrate which allows an analyte to be detected through surface-enhanced Raman spectroscopy. For example, the substrate 11 may be a solid substrate. Herein, glass, plastic, silicon, or the like is used, which are inexpensive and readily available. The substrate 31 may have a diameter of approximately 1 mm and a thickness of approximately 0.1 to 0.5 mm.

On the substrate 31, a metal pattern 14 is formed. There is no particular limitation as to the metal pattern 14, so long as it is made of a substance that exhibits a plasmon. As the metal pattern 14, precious metals alone, e.g., Au, Ag, Cu, or Pt, or an intermetallic compound, alloy, or the like that is composed of such elements, can be used.

The metal pattern 14 may be a metal pattern layer which has been patterned by using a lithography technique, an imprint technique, or the like. The metal pattern formed on the substrate 11 may be a metal film having metal particles, gold nanorods, minute protrusions and depressions, or the like, for example. The metal pattern may be of any structure that causes surface-enhanced Raman scattering.

On the metal pattern 14, a layer of phenylboronic acid compound 15 is formed as the proximate substance. As the phenylboronic acid compound 15, any substance can be used which reversibly reacts with glucose, such that the resultant surface-enhanced Raman-scattered light has at least one peak whose intensity varies with changes in the concentration of glucose. The phenylboronic acid compound 15 may be chemisorbed to the metal pattern layer 14 via a thiol group at one end thereof.

The phenylboronic acid compound as the proximate substance may be a compound expressed by General Formula (1) below (where n is an integer of 1 or more).

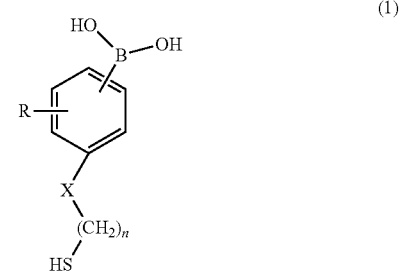

(1)

Examples of the divalent linking group indicated as X include linking groups that contain at least one, or two or more bonds among the alkyl bond, the amide bond, the carbamoyl bond, the ether bond, the ester bond, the thioester bond, the thioether bond, the sulfonamide bond, the urethane bond, the sulfonyl bond, the imine bond, the urea bond, the thiourea bond, and the like.

It is advantageous when the n value in General Formula (1) is from 3 to 16. In this range, it is easy to form on the metal pattern 14 a self-assembled monolayer which is composed of long-chain molecules having a thiol group added at one end of the hydrocarbon chain.

Examples of R in General Formula (1) include a hydrogen atom, a hydroxy group, a halogen group, a carboxyl group, a carboxylic acid ester group, a carboxylic acid amide group, a cyano group, a nitro group, an amino group, and an alkoxy group with 1 to 5 carbons. R in General Formula (1) is not limited to the above.

Since the sensor chip 10 shown in FIG. 1 may be embedded in a biological body, coating with a polymer which has low bioactivity (i.e., a biocompatible polymer) may be provided around the sensor chip 10. This confers biocompatibility to the sensor chip, and precludes (or minimizes) interactions of nonspecific proteins with the chip surface as well as inflammatory responses.

The biocompatible polymer 13 (second biocompatible polymer) shown in FIG. 1 is a material which is not biodegradable. The biocompatible polymer 13 may contain polydimethylsiloxane (PDMS), parylene C, parylene HT, polycarbonate, polyolefin, polyurethane, acrylonitrile copolymer, a copolymer of polyvinyl chloride, polyamide, polysulfone, polystyrene, vinyl fluoride resin, polyvinyl alcohol, polyvinyl ester, polyvinyl butyrate, polyvinyl acetate, polyvinylidene chloride, polyvinylidene fluoride, polyimide, polyisoprene, polyisobutylene, polybutadiene, polyethylene, polyether, polytetrafluoroethylene, polychloroether, polymethyl methacrylate, polybutylmethacrylate, nylon, cellulose, or silicone rubber, although this is not a limitation.

[0112-0113] The light scattering layer 12 is formed on the side of the substrate 11 that is irradiated with excitation light. The light scattering layer 12 is made of a first biocompatible polymer. The first biocompatible polymer is biodegradable. As used herein, to be "biodegradable" means having the capability of being promptly catabolized in vivo to be degraded and disappear.

Examples of biodegradable first biocompatible polymers include polylactic acid, polyglycolic acid, poly(lactic-co-glycolic acid), poly(lactide-co-glycolide), poly(ethyleneglycol-lactide), poly(glycolic acid-caprolactone), lactic acid-ethyleneglycol copolymer, polycaprolactone, poly(lactide-co-caprolactone), polyhydroxybutyrate, polyhydroxy isobutyrate, polyvalerolactone, poly γ-hydroxy valeric acid, poly(hydroxybutyrate-hydroxyvalerate), polyisobutyl-cyano acrylate, and polyalkyl-cyano acrylate. Without being limited to the above, the first biocompatible polymer may be chitin, chitosan, gelatin, or the like.

High-molecular weight polymer for use in the embodiment of the present invention which are biocompatible or capable of being degraded within a biological body are easily available, or easily synthesized by generic synthesis techniques. Moreover, they lack C—S bonds within the molecule, as will be described later.

The light scattering layer 12 may be constructed so as to include the first biocompatible polymer and air voids dispersed in the polymer. Providing the light scattering layer 12 prevents the biological tissue from coming into direct contact with the sensor plane when the sensor chip 10 is embedded in a biological body, for example. Thus, it provides cushioning effects against the impact, shear stress, etc., upon contact.

Since the light scattering layer 12 is made of a biocompatible material which is biodegradable, it can be degraded in vivo when the sensor chip 10 is embedded in a biological body. When the light scattering layer 12 includes air voids, it is more easily degraded and degraded in a shorter amount of time in vivo than in a structure where the light scattering layer 12 lacks air voids.

Although there is no particular limitation to the thickness of the light scattering layer 12, it is advantageously not less than 1 μm and not more than 1000 μm. If it is 1 μm or less, the sensor plane is likely to be damaged upon contact with the biological tissue during embedment into a biological body. If it is 1000 μm or more, degradation by biological fluids takes time when embedded in a biological body, and it may take longer until a sensor function expresses itself.

With the light scattering layer 12 being present on the sensor plane as shown in FIG. 1, when the sensor surface is irradiated with excitation light, the light scattering effect of the light scattering layer 12 either prevents the excitation light from reaching the sensor surface or heavily attenuates the excitation light, so that no first surface-enhanced Raman-scattered light that is ascribable to the phenylboronic acid compound occurs. Once the light scattering layer 12 is degraded in vivo, first surface-enhanced Raman-scattered light will occur.

<Step (d)>

Step (d) is a step of detecting first surface-enhanced Raman-scattered light, generated at step (c), with the detector to obtain a first intensity Xa. Hereinafter, step (d) according to Embodiment 2 will be described in detail.

Figure 3:
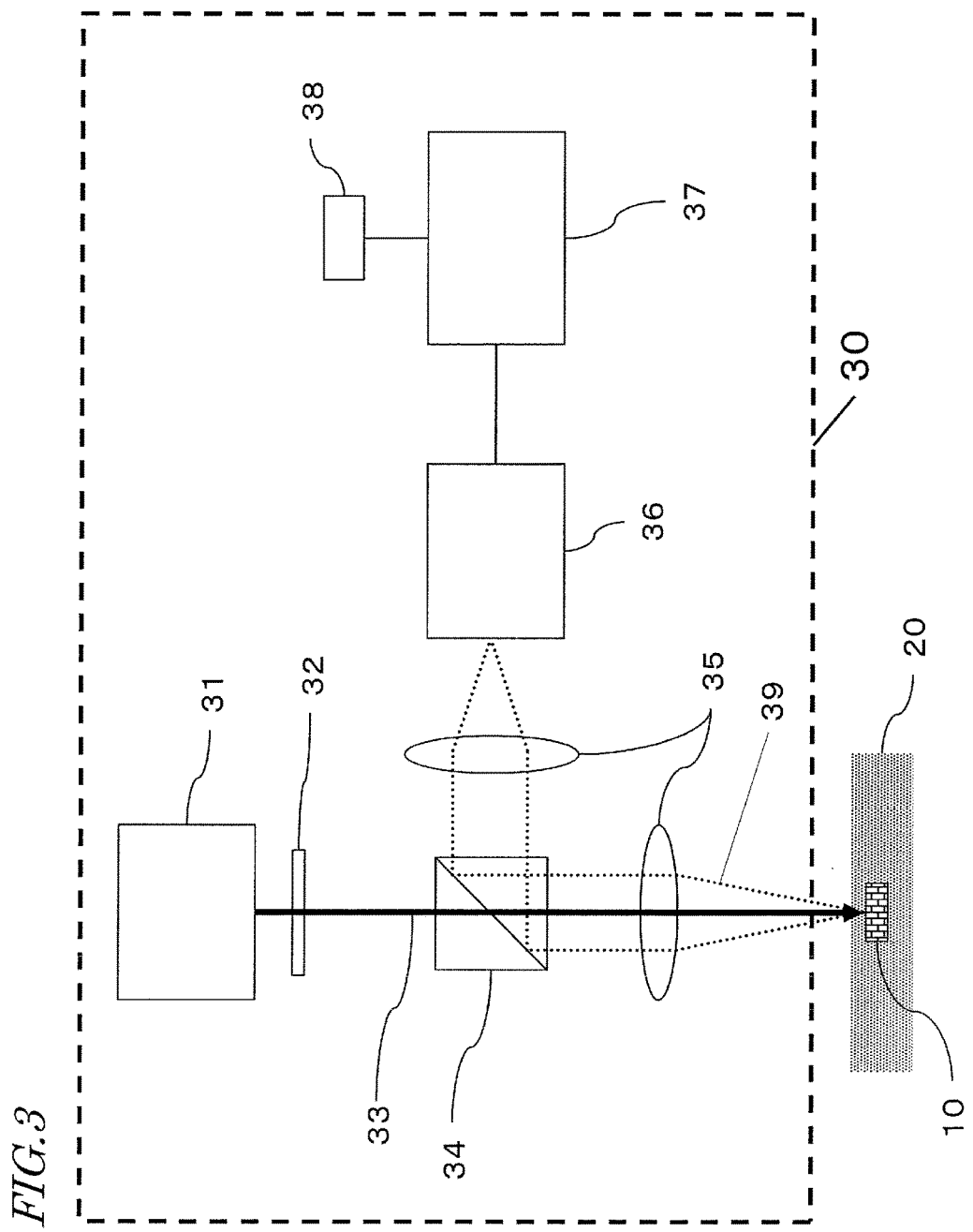
FIG. 3 is a diagram showing an exemplary construction for a detection apparatus according to Embodiment 2.

As shown in FIG. 3, when the sensor chip 10 is irradiated with excitation light 33 from the light source 31, a surface plasmon resonance occurs around the metal pattern 14, whereby the electric field in the vicinity of the metal pattern 14 is enhanced. This causes enhancement of Raman-scattered light from any substance that is located in the vicinity of the metal pattern 14 (within 0.5 to 30 nm).

The surface-enhanced Raman-scattered light 39 is shaped by the optical lens system 35, reflected by the beam splitter 34, and subjected to further shaping by the optical lens system 35, and thereafter detected by the spectrometer 36.

As the spectrometer 36, any known technique can be used without limitation, e.g., Czerny-Turner spectrographs, Echelle spectrographs, flat-field spectrographs, and filter spectrographs.

As described earlier, the intensity of surface-enhanced Raman-scattered light is $10^4$ to $10^9$ times greater than the intensity of usual Raman-scattered light. Therefore, the surface-enhanced Raman-scattered light that occurs in the vicinity of the metal pattern 14 has a far greater intensity than that of Raman-scattered light occurring in skin tissue (epidermal tissue 21, dermis tissue 22). This means that Raman-scattered light from the vicinity of the metal pattern 14 is selectively enhanced.

Figure 4:
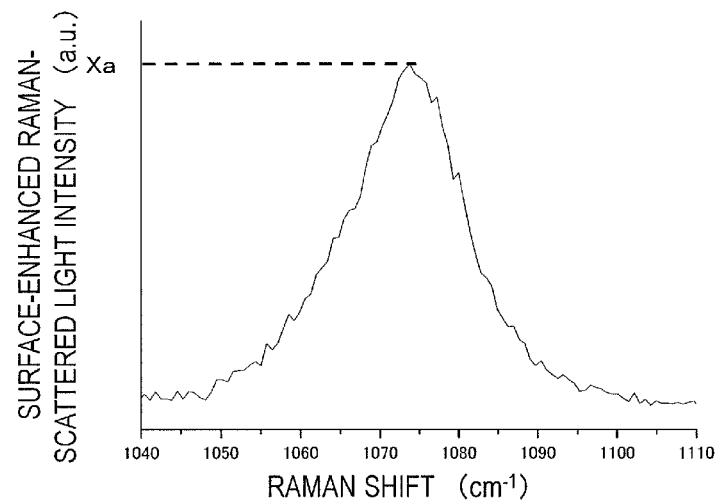
FIG. 4 is an illustrative spectrum chart of first surface-enhanced Raman-scattered light.

FIG. 4 is an illustrative spectrum chart of the first surface-enhanced Raman-scattered light. In the example shown in FIG. 4, a peak of first surface-enhanced Raman-scattered light that is ascribable to the C—S bond in the phenylboronic acid compound 15, which has been chemisorbed onto the metal pattern 14, is observed at 1076 $cm^{-1}$. In FIG. 4, the signal intensity (e.g., intensity at the peak position) of first surface-enhanced Raman-scattered light is indicated as Xa.

International Publication No. 2011/053247 indicates that, when glucose is bound to a phenylboronic acid compound or a derivative thereof, a change occurs in the intensity of surface-enhanced Raman-scattered light due to electronic and/or steric changes.

However, the C—S bond corresponding to the first surface-enhanced Raman-scattered light is located at the most distant place from the boronic acid group to which glucose binds, and therefore does not undergo any changes in the electron distribution within the molecule. Furthermore, the thiol group (—SH) is bound (via a covalent bond) to the metal pattern 14, and therefore does not undergo any structural changes through binding of glucose. Therefore, the first surface-enhanced Raman-scattered light does not vary with changes in the concentration of the analyte. In other words, a first intensity Xa is obtained by detecting first surface-enhanced Raman-scattered light from the proximate substance (which herein is the phenylboronic acid compound 15) with the detector.

Note that the first biocompatible polymer composing the light scattering layer 12 provided near the metal pattern similarly exhibits a peak of surface-enhanced Raman-scattered light. However, the first biocompatible polymer lacks the C—S bond. Therefore, a peak of the surface-enhanced Raman-scattered light from the first biocompatible polymer will not overlap a peak of the surface-enhanced Raman-scattered light that is ascribable to the C—S bond in the phenylboronic acid compound 15 serving as an example of the proximate substance.

\<Step (e)\>

Step (e) is a step of determining, with the calculation circuit, whether or not the first intensity Xa is equal to or greater than a predetermined intensity Xz. Hereinafter, step (e) in Embodiment 2 will be described in detail.

The calculation circuit 37 compares a first surface-enhanced Raman-scattered light intensity (Xa), as detected by the spectrometer 36, against a predetermined intensity Xz which has been defined in advance. The detection apparatus 30 may retain the predetermined intensity Xz in the memory 38 in advance.

When the first intensity Xa is lower than the predetermined intensity Xz, it is indicative that the light scattering layer 12 exists on the sensor surface. That is, since the first biocompatible polymer composing the light scattering layer 12 formed on the sensor surface exists on the sensor plane, glucose in the biological body (which exemplifies the analyte) cannot react with the phenylboronic acid compound 15. That is, a sensor function has not expressed itself.

When the first intensity Xa becomes higher than the predetermined intensity Xz after a lapse of time, it is indicative that the light scattering layer 12 has disappeared from the sensor surface, i.e., a sensor function has expressed itself. In other words, by measuring the intensity of first surface-enhanced Raman-scattered light that is ascribable to the C—S bond in the phenylboronic acid compound 15, it is possible to know that the light scattering layer 12 on the sensor chip 10 being embedded e.g. in a biological body has disappeared, and that a sensor function has thus expressed itself.

\<Steps (f) and (g)\>

Step (f) is a step of, after it is determined in step (e) that the first intensity Xa has become equal to or greater than the predetermined intensity Xz, irradiating the sensor chip embedded inside the subject with excitation light from the light source, thereby generating second surface-enhanced Raman-scattered light. Step (g) is a step of detecting with the detector the second surface-enhanced Raman-scattered light that occurred in step (f) to obtain a second intensity Xb. Hereinafter, steps (f) and (g) in Embodiment 2 will be described in detail.

Figure 5:
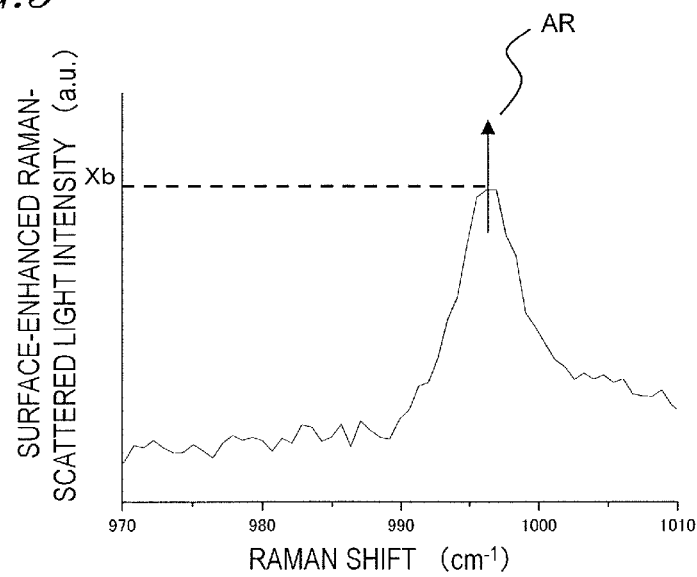
FIG. 5 is an illustrative spectrum chart of second surface-enhanced Raman-scattered light.

FIG. 5 is an illustrative spectrum chart of second surface-enhanced Raman-scattered light. In the example shown in FIG. 5, a peak of second surface-enhanced Raman-scattered light is observed at 997 $cm^{-1}$. As is clear from a comparison between FIG. 4 and FIG. 5, the peak position of the second surface-enhanced Raman-scattered light differs from the peak position of the first surface-enhanced Raman-scattered light. The second surface-enhanced Raman-scattered light is ascribable to a benzene ring in the phenylboronic acid compound 15, which has been chemisorbed onto the metal particles in the metal pattern 14 (which may include e.g. metal particles). In FIG. 5, the signal intensity of the second surface-enhanced Raman-scattered light (e.g., intensity at the peak position) is indicated as Xb.

The second surface-enhanced Raman-scattered light is a signal that is ascribable to a benzene ring to which a boronic acid group, which binds to glucose, is directly bound. Therefore, as is disclosed in International Publication No. 2011/053247, supra, due to binding of glucose, the second surface-enhanced Raman-scattered light is affected by electronic and/or steric changes within the molecule. In other words, the second surface-enhanced Raman-scattered light is light that has occurred from the proximate substance having bound to the analyte, e.g., glucose, through irradiation of excitation light from the light source. Therefore, the second surface-enhanced Raman-scattered light varies with changes in the concentration of the analyte.

In other words, a second intensity Xb is obtained by detecting with the detector the second surface-enhanced Raman-scattered light from the proximate substance having bound to the analyte (which herein is the phenylboronic acid compound 15 having bound to glucose). As schematically shown in FIG. 5 by an arrow AR, the second surface-enhanced Raman-scattered light becomes enhanced when the analyte (e.g., glucose) exists. In other words, in this example, the second surface-enhanced Raman-scattered light varies with changes in the glucose concentration.

After the second intensity Xb is obtained, the calculation circuit 37 may calculate the concentration of the analyte based on accurate information which represents correlation between the peak intensity Xb and the analyte (e.g., glucose) concentration. This makes it possible to measure the concentration of the analyte (e.g., glucose) which is contained in a biological body, for example.

The information representing correlation between the peak intensity Xb and the analyte concentration may be a calibration curve, for example. In this case, by using the peak intensity Xb as an input value, the calculation circuit 37 may rely on a mathematical function representing the calibration curve to calculate an analyte concentration value corresponding to the input value Xb. In the memory 38, the detection apparatus 30 may previously store information representing correlation between the peak intensity Xb and the analyte concentration. For example, the detection apparatus 30 may previously store in the memory 38 parameters of a mathematical function representing the calibration curve, etc.

Thus, by using the sensor chip of Embodiment 2 and the detection method associated therewith, it is also possible to measure the concentration of an analyte (e.g., glucose) which is present in a biological body. Note that the respective steps described above can be executed through control under instructions from the calculation circuit 37.

Embodiment 3

Embodiment 3 will be described with reference to FIG. 8. In Embodiment 3, a detection apparatus for detecting an analyte by using the sensor chip 110 described in Embodiment 1 is proposed.

FIG. 8 is a diagram showing a detection apparatus 130 according to Embodiment 3. The detection apparatus 130 of Embodiment 3 is a detection apparatus which detects an analyte by using the sensor chip 110 described in Embodiment 1. The detection apparatus 130 includes a light source 131 which emits excitation light, a detection section 140 which detects scattered light, and a calculation section 137.

The detection apparatus 130 irradiates the sensor chip 110, which is e.g. embedded inside a subject 200, with excitation light from the light source 131 to generate first surface-enhanced Raman-scattered light. The detection apparatus 130 detects the generated first surface-enhanced Raman-scattered light with the detection section 140, thereby obtaining a first intensity Xa.

At this point, the detection apparatus 130 determines whether or not the first intensity Xa is equal to or greater than a predetermined intensity Xz by using the calculation section 137. After it is determined that the first intensity Xa has become equal to or greater than the predetermined intensity Xz, the detection apparatus 130 irradiates the sensor chip 110, which is e.g. embedded inside a subject, with excitation light from the light source 131 to generate second surface-enhanced Raman-scattered light. The detection apparatus 130 detects the generated second surface-enhanced Raman-scattered light with the detection section 140, thereby obtaining a second intensity Xb.

With the above construction, by utilizing scattered light from the proximate substance 115, it can be determined whether the light shielding layer 112 has been degraded inside the subject or not. Since the second intensity Xb is obtained after conforming that the light shielding layer 112 has been degraded inside the subject, a more accurate analyte detection is made. In other words, obtaining a second intensity Xb after confirming that the first intensity Xa has become equal to or greater than the predetermined intensity Xz ensures a more accurate analyte detection. Note that irradiation of excitation light for generating second surface-enhanced Raman-scattered light may precede the determination that the first intensity Xa has become equal to or greater than the predetermined intensity Xz, so long as the determination that the first intensity Xa has equal to or greater than the predetermined intensity Xz is made before the second intensity Xb is obtained.

The detection apparatus 130 of Embodiment 3 may include a memory for retaining information representing correlation between the second intensity Xb and the analyte concentration (e.g., a calibration curve). In this case, an analyte concentration may be calculated based on the information representing correlation with the second intensity Xb (e.g. a calibration curve) that has been obtained by detecting the generated second surface-enhanced Raman-scattered light with the detection section. This construction will enable a more accurate measurement of the analyte concentration.

As a more specific exemplary construction for the detection apparatus 130 of Embodiment 3, the detection apparatus 30 described in Embodiment 2 may be adopted, for example. In other words, the light source 131 may be composed of the light source 31 and the like. The detection section 140 may be composed of the spectrometer 36 and the like. The calculation section 137 may be composed of the calculation circuit 37 and the like.

The detection apparatus of Embodiment 3 is able to detect an analyte by being controlled according to the detection method described in Embodiment 2. The detection method described in Embodiment 2 may be executed based on instructions from the calculation section 137, for example. For example, the detection method described in Embodiment 2 may be performed through control under instructions from a calculation circuit 37 constituting a part of a computer.

In the case where obstructing components such as proteins in the biological body exist in the vicinity of the metal pattern, surface-enhanced Raman-scattered light (hereinafter referred to as obstructing Raman-scattered light) may similarly occur from the obstructing components. However, when the analyte is glucose and the proximate substance is a phenylboronic acid compound, for example, no peaks of obstructing Raman-scattered light will exist in regions near the respective peak positions of first surface-enhanced Raman-scattered light and second surface-enhanced Raman-scattered light. Thus, glucose detection errors associated with obstructing components can be reduced.

Although Embodiments 1 to 3 above each illustrate a light scattering layer which scatters excitation light, the light shielding layer is not limited to this example. The light shielding layer may be a light reflecting layer that reflects excitation light, for example. Alternatively, the light shielding layer may be a light absorbing layer which absorbs excitation light, for example. The light shielding layer may be of any construction so long as it blocks excitation light from going into the proximate substance and is degraded inside the subject.

In Embodiments 1 to 3, the subject may be a human or animal body. The subject may be inanimate. That is, the sensor chip may be placed in a subject solution, for example. In this case, the above-described detection method or detection apparatus may be used to detect the analyte being contained in the subject solution. The subject solution may be a fluid which is extracted from a biological body. The subject solution may be, for example, blood, sweat, tears, urine, saliva, or the like.

An embodiment of the present invention can be used for detecting an analyte in, for example, a biological body (e.g., a biological component such as glucose), or measuring the concentration thereof.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A sensor chip for detecting an analyte inside a subject, comprising
    a substrate, a metal pattern, a proximate substance, and a light shielding layer,
    the metal pattern being on one face of the substrate, and
    the proximate substance being on or near the metal pattern, wherein,
    the metal pattern induces a surface plasmon wave by being irradiated with excitation light;
    the proximate substance generates first surface-enhanced Raman-scattered light by being irradiated with the excitation light, the first surface-enhanced Raman-scattered light having a first peak;
    the first surface-enhanced Raman-scattered light does not vary with changes in the concentration of the analyte;
    the proximate substance is a substance which binds to the analyte;
    the proximate substance having bound to the analyte generates second surface-enhanced Raman-scattered light by being irradiated with the excitation light, the second surface-enhanced Raman-scattered light having a second peak different from the first peak;
    the second surface-enhanced Raman-scattered light varies with changes in the concentration of the analyte;
    the light shielding layer is provided on the substrate so as to cover the metal pattern and the proximate substance;
    the light shielding layer is a layer which blocks the excitation light from going into the proximate substance; and
    the light shielding layer is made of a substance which becomes degraded inside the subject.

2. The sensor chip of claim 1, wherein air voids are dispersed in the light shielding layer.

3. The sensor chip of claim 1, wherein the analyte is glucose.

4. The sensor chip of claim 3, wherein,
    the proximate substance is a phenylboronic acid compound having a thiol group at one end; and
    the phenylboronic acid compound is chemisorbed to a surface of the metal pattern via the thiol group.

5. The sensor chip of claim 4, wherein,
the first peak of the first surface-enhanced Raman-scattered light has the peak position 1073 cm$^{-1}$; and
the second peak of the second surface-enhanced Raman-scattered light has the peak position 997 cm$^{-1}$.

6. The sensor chip of claim 1, wherein,
the subject is a biological body; and
the light shielding layer is made of a first biocompatible polymer which is biodegradable.

7. The sensor chip of claim 1, wherein,
the subject is a biological body; and
another face of the substrate not having the metal pattern thereon is coated with a second biocompatible polymer which is not biodegradable.

8. The sensor chip of claim 1, wherein the light shielding layer is a light scattering layer which scatters the excitation light.

9. A detection method for detecting the analyte by using the sensor chip of claim 1, comprising the following steps (a) to (g):
step (a) of providing a detection apparatus,
the detection apparatus including a light source for emitting the excitation light, a detector, and a calculation circuit;
step (b) of embedding the sensor chip inside a subject;
step (c) of irradiating the sensor chip embedded inside the subject with the excitation light from the light source to generate first surface-enhanced Raman-scattered light;
step (d) of detecting the first surface-enhanced Raman-scattered light occurring at step (c) with the detector to obtain a first intensity Xa;
step (e) of determining with the calculation circuit whether or not the first intensity Xa is equal to or greater than a predetermined intensity Xz;
step (f) of, after determining at step (e) that the first intensity Xa is equal to or greater than the predetermined intensity Xz, irradiating the sensor chip embedded inside the subject with the excitation light from the light source to generate second surface-enhanced Raman-scattered light; and
step (g) of detecting the second surface-enhanced Raman-scattered light occurring at step (f) with the detector to obtain a second intensity Xb.

10. The detection method of claim 9, wherein,
the detection apparatus further includes a memory for retaining information representing correlation between the second intensity Xb and analyte concentration; and
a concentration of the analyte is calculated based on the second intensity Xb obtained at step (g) and on the information.

11. A detection apparatus for detecting the analyte by using the sensor chip of claim 1, comprising:
a light source for emitting the excitation light, a detector, and a calculation circuit, wherein,
the detection apparatus irradiates the sensor chip embedded inside a subject with the excitation light from the light source to generate first surface-enhanced Raman-scattered light,
the detector detects the generated first surface-enhanced Raman-scattered light to obtain a first intensity Xa,
the calculation circuit determines whether or not the first intensity Xa is equal to or greater than a predetermined intensity Xz;
after determining that the first intensity Xa is equal to or greater than the predetermined intensity Xz, the detection apparatus irradiates the sensor chip embedded inside the subject with the excitation light from the light source to generate second surface-enhanced Raman-scattered light; and
the detector detects the generated second surface-enhanced Raman-scattered light to obtain a second intensity Xb.

12. The detection apparatus of claim 11, wherein,
the detection apparatus further comprises a memory for retaining information representing correlation between the second intensity Xb and analyte concentration; and
the detection apparatus calculates a concentration of the analyte based on the second intensity Xb obtained by detecting the generated second surface-enhanced Raman-scattered light with the detector and on the information.

* * * * *